United States Patent [19]
Casas-Perez et al.

[11] Patent Number: 5,458,875
[45] Date of Patent: Oct. 17, 1995

[54] IN OVO METHOD FOR DELIVERING LACTOBACILLUS REUTERI TO THE GASTROINTESTINAL TRACT OF POULTRY

[75] Inventors: Ivan A. Casas-Perez; Frank W. Edens, both of Raleigh, N.C.

[73] Assignee: Biogaia AB, Stockholm, Sweden

[21] Appl. No.: 347,849

[22] Filed: Dec. 1, 1994

Related U.S. Application Data

[63] Continuation of Ser. No. 81,837, Jun. 22, 1993, abandoned, which is a continuation of Ser. No. 646,879, Jan. 28, 1991, abandoned, which is a continuation-in-part of Ser. No. 539,014, Jun. 15, 1990, abandoned.

[51] Int. Cl.$^6$ .................. A61K 31/00; A61K 35/00; C12N 1/20
[52] U.S. Cl. .................. 424/93.45; 424/93.4; 435/252.1; 435/252.9; 119/6.8
[58] Field of Search .................. 424/93.4, 93.45; 435/252.1, 252.9; 119/6.8

[56] References Cited

U.S. PATENT DOCUMENTS

| | | | |
|---|---|---|---|
| 4,040,388 | 8/1977 | Miller et al. | 119/1 |
| 4,314,995 | 2/1982 | Hata et al. | 424/93 J |
| 4,335,107 | 6/1982 | Snoeyenbos et al. | 424/93 C |
| 4,469,047 | 9/1984 | Miller et al. | 119/1 |
| 4,593,646 | 6/1986 | Miller et al. | 119/1 |
| 4,681,063 | 7/1987 | Hebrank | 119/1 |
| 4,903,635 | 2/1990 | Hebrank | 119/1 |
| 4,946,791 | 8/1990 | Manfredi et al. | 435/252.9 |
| 4,980,164 | 12/1990 | Manfredi et al. | 424/93 |
| 5,206,015 | 4/1993 | Cox et al. | 424/93 C |

OTHER PUBLICATIONS

Sell, Basic Immunology: Immune Mechanisms in Health and Disease, published 1987, pp. 3–7.
Tuzard, Veterinary Immunology: An Introduction, Third Edition, published 1987, pp. 185–199.
Edens et al., "lactobacillus Reuteri and They Reduce Salmonella colonization in the Ceca of Turkey Poults", Presented at Southern Poultry Science Society Annual Mating, Jan. (28–29), 1991, pp. 1–8.
Cox et al., Poultry Science, vol. 69, Suppl. 1, (1990) p. 162.
Axelsson et al., J. Appl. Bacteriol., vol. 62, pp. 433–440 (1987).
Axelsson et al., Microbiol Ecol. Health Dis., vol. 2, pp. 131–136 (1989).
Chung et al., Microbiol Ecol. Health Dis., vol. 22, pp. 137–144 (1989).
Dellaglio et al., Zbl. Bakt. Hyg., Abt. Oreg. C2:349–356 (1981).
Dobrogosz et al., The Regulatory & Protective Role of the Normal Microflore, edited by Grubb et al., pp. 283–292 (1989).
Food & Drug Adminstration Compliance Policy Guide No. 7126.41 (May 2, 1988).
Fox, S., Vet. Med., pp. 806–830, (Aug. 1988).
Fuller, J. Appl. Bacteriol. Symp. Suppl., 15–75 (1986).
Kandler et al., Zbl. Bakt. Hyg. Abt. oreg., C1:264–269 (1980).
Kandler et al., Bergey's Manual of Systemetic Bacteriology, vol. 2, pp. 1208–1234 (1986).
Mead et al., J. of Applied Bacteriology Symposium Supplement, pp. 675–755 (1986).
Orla–Jansen, S., Det. Kongelige Danske Vidensbkbern Selskab., Biologiski Skrigter, BindII, No. 3 (1943).
Parker, R. B., Anim. Nutr. Health, vol. 29, pp. 4–8 (1974).
Parkhurst et al., International Poultry Trade Show SE Poultrys Egg Assn. Altanta, Ga., Abs. Sci. Mat. (1991).
Sissons, J. W., J. Sci. Food Agric., vol. 46, pp. 1–13 (1989).
Talarico et al., Antimicrob. Agents Chemoterap., vol. 33, pp. 674–679 (1989).
Talarico et al. Antimicrob Agents Chemoterap., vol. 32, pp. 1854–1858 (1988).
Talarico et al., Appl. Environ. Microbiol., vol. 56 pp. 1195–1197 (1990).
Talarico et al., Appl. Environ. Microbiol., vol. 56 pp. 943–948 (1990).
Tortuero et al., Poultry Science, vol. 52, pp. 197–203 (1973).
Fuller, Br. Poultry Sci, vol. 18, pp. 85–94 (1977).

*Primary Examiner*—Marian C. Knode
*Assistant Examiner*—Susan M. Dadio
*Attorney, Agent, or Firm*—Olive & Olive

[57] ABSTRACT

A method of establishing direct feed microorganisms such as *Lactobacillus reuteri* in the gastrointestinal tract of avian organisms in which eggs are inoculated with living cells of the microorganism.

3 Claims, No Drawings

IN OVO METHOD FOR DELIVERING LACTOBACILLUS REUTERI TO THE GASTROINTESTINAL TRACT OF POULTRY

This application is a continuation of U.S. application Ser. No. 08/081,837, filed on Jun. 22, 1993, now abandoned, which is a continuation of U.S. application Ser. No. 07/646,879, filed on Jan. 28, 1991, now abandoned, which is a continuation-in-part of U.S. application Ser. No. 07/539,014, filed on Jun. 15, 1990, now abandoned.

FIELD OF INVENTION

This invention relates to a new method for delivering viable microbial cells to animals in ovo.

BACKGROUND INFORMATION

The terms "probiotics" is attributed to Parker (20) who defined them as "organisms and substances which contribute to intestinal balance" when used as dietary supplements. This publication and all other publications and patents cited herein are incorporated herein by reference. Later, Fuller (11) considered this definition to be too broad since, in addition to including cell cultures and microbial metabolites, it could encompass antibiotic preparations. More recently, a number of summaries have appeared in the literature describing the scientific basis for use of probiotics as intestinal inoculants for production animals (10, 26). It has been suggested that the term "probiotics" be replaced by the term "direct feed microorganisms," or DFM's (9).

The concept of adding viable, harmless lactic acid bacteria to the gastrointestinal tract as a dietary supplement was first appreciated by Metchnikoff (16) who viewed the consumption of yoghurt by Bulgarian peasants as conferring a long span of life. Some workers have claimed that the therapeutic value derived from ingestion of such fermented milk products is related to the viable bacteria present in these products (12, 27). Since Metchnikoff's early reports, several studies have shown the ability of lactobacilli, for example, to suppress coliform growth. Feeding viable *Lactobacillus acidophilus* cells to young dairy calves was shown to reduce the incidence of diarrhoea (3), and increase the numbers of lactobacilli and reduce coliform counts in feces (4). These findings contrast with those of others who were unable to demonstrate benefits from feeding either *Lactobacillus acidophilus* (8, 13) or milk cultured with *Lactobacillus acidophilus* or *Lactobacillus lactis* (17).

In a detailed study by Muralidhara et. al. (18), piglets given a *Lactobacillus lactis* concentrate for up to 8 weeks after birth showed a progressive decline in coliform counts in fecal samples. Scouring in these animals was negligible, but was evident in control pigs especially at weaning. Underdahl et al. (32) observed only mild diarrhoea lasting 2-4 days in gnotobiotic pigs inoculated with *Streptococcus faecium* prior to artificial *Escherichia coli* infection. In the same study, persistent diarrhoea occurred in pigs similarly infected with *Escherichia coli*, but without prophylactic treatment with the Streptococcus microorganism.

Probiotics (hereafter referred to as DFM's) are bacterial or yeast preparations that are administered orally or added to feeds. The most commonly used DFM's are strains of the lactic acid bacteria (LAB), particularly those classified in the following genera: Lactobacillus, Lactococcus, and Enterococcus. Included among these are the following species: *Lactobacillus acidophilus, Lactobacillus bulgaricus, Lactobacillus plantarum, Lactobacillus casei, Lactobacillus lactis, Lactococcus lactis, Lactococcus thermophilus, Lactococcus diacetylactis,* and *Enterococcus faecium*. Besides these LAB, some species of Bacillus (*Bacillus subtilis, Bacillus toyoi*) and yeasts and molds (*Saccharomyces cerevisiae, Aspergillus oryzae,* and Torulopsis sp.) are used as DFM's (10).

It is generally held that during periods of low resistance, such as stress, undesirable microorganisms are able to proliferate in the GI tract of animals, humans included. Maintaining a normal, healthy balance of microorganisms is deemed to be critical during such stressful periods (10). The concept underlying use of DFM's, therefore is that if sufficient numbers of an appropriate microorganism(s) are introduced into the intestinal tract (i) at times of stress and/or disease, (ii) at birth, or (iii) after antibiotic treatment (when minimal LAB are present), the negative consequences of the microbial imbalances can be minimized or overcome. Using such preparations of live, naturally occurring microorganisms helps restore and maintain the proper balance of beneficial microbes in the GI tract during times of stress, disease, and following antibiotic therapy (10). This concept, descriptions of proposed modes of action, and evidence for the efficacious uses of DFM's for all production animals are summarized in reviews by Fox (10), Sissons (26), and by various authors (22).

One of the major problems or limitations encountered in commercial scale application of DFM's to animals is (i) the availability of suitable delivery systems, and (ii) the ability to get the probiotic preparations to the animals as quickly as possible after birth. This is particularly true when pelletized feeds are used, as is the case in the poultry industry. The pelletization process generally includes one or more heating steps involving temperatures high enough to pasteurize or sterilize the feed components, thereby precluding incorporation of viable microorganisms into these feeds prior to pelletization.

The present invention describes novel methods and processes for overcoming some of these problems, by delivering viable DFM's in ovo. The DFM used to develop these methods is *Lactobacillus reuteri*. This species was chosen because it has demonstrated efficacy as a DFM in poultry (21). Previous patent applications have been submitted relating to unique properties of the species. These applications are: PCT/U.S. 88/01423, filed Apr. 28, 1988 and published Nov. 3, 1988, claiming priority from U.S. Ser. No. 07/268,361 filed Sep. 19, 1988 which is a continuation-in-part of U.S. Ser. No. 07/102,830 filed Sep. 22, 1987 which is a continuation-in-part of U.S. Ser. No. 07/046,027 filed May 1, 1987; and U.S. Ser. No. 07/539,014 filed Jun. 15, 1990. The disclosure of these applications is incorporated herein by reference.

*Lactobacillus reuteri* is a species of lactic acid bacteria recognized since the turn of the century (19). Originally assigned different species names (e.g., *Lactobacillus fermentum* biotype II), it obtained distinct species status in 1980 and is registered in the 1988 edition of Bergey's manual (14, 15). It is found in foods, particularly dairy products and meats, but exists primarily in the GI tract of healthy animals, including humans (1, 6, 7, 14, 15, 23, 24, 25, 33).

*Lactobacillus reuteri* is the dominant heterofermentative Lactobacillus inhabiting the GI tract (23, 24, 25). It is a typical heterofermenter, converting sugars into acetic acid, ethanol, and $CO_2$ in addition to lactic acid which is the major endproduct of homofermentative metabolism carried out by species such as *Lactobacillus acidophilus* (31). It utilizes the phosphoketolase pathway for conversion of glucose to end-products. When glycerol, an alternate hydrogen acceptor, is present in the culture medium together with glucose or other utilizable carbon and energy sources (e.g., lactose), acetate rather than ethanol accumulates, and the glycerol is reduced to 1,3-propanediol via the metabolic intermediate, 3-hydroxypropionaldehyde (3-HPA). 3-HPA has been shown to have potent antimicrobial activity, and *Lactobacillus reuteri* appears to be unique among microorganisms examined to date in its ability to secrete this substance, termed reuterin, into the surrounding medium (2, 5, 7, 28, 29, 30, 31). This unique antimicrobial activity may play a role in competitive survival of this species in the gastrointestinal ecosystem, and/or its ability to regulate growth and activities of other microorganisms in this ecosystem (7). It is thus very important to establish this microorganism early in animals. It is therefore an object of the invention to provide a method for delivering DFM's, such as Lactobacillus, to avian species.

Other objects and advantages will be more fully apparent from the following disclosure and appended claims.

SUMMARY OF INVENTION

Pure cultures of *Lactobacillus reuteri* are injected into eggs with no detrimental effect on their hatchability. The invention generally provides a means for delivering lactobacilli and other DFM's into eggs of avian species, so that these microorganisms may be well established in the bird gastrointestinal system at hatching time.

Other aspects and features of the invention will be more fully apparent from the following disclosure and appended claims.

DETAILED DESCRIPTION OF THE INVENTION AND PREFERRED EMBODIMENTS THEREOF

The present invention provides a method of providing DFM's to avian embryos in the eggs so that the DFM's are established in the gastrointestinal tract of the newly hatched birds. Using methods of delivery previously developed for delivery of antibiotics (see U.S. Pat. Nos. 4,681,063 and 4,903,635, for example) or a manual needle puncture of the egg into the air cell, live cells of a DFM culture, for example, *L. reuteri* are delivered into the air cell in incubating eggs.

The features and advantages of the present invention will be more clearly understood by reference to the following example, which is not to be construed as limiting the invention.

EXAMPLE

Eggs of turkeys (Nicholas) or chickens are aseptically punctured above the air cell with a needle, preferably about 2 days before hatch. With a syringe and needle, 100 ul of a suspension of *Lactobacillus reuteri*, strain T-1 (isolated from turkeys) or strain 11284 (isolated from chickens), containing about $10^5$, $10^7$, or $10^8$ cells of the strain, is injected into the air cell. Each of these strains has been deposited with the American Type Culture Collection in Rockville, Md. Table 1 shows the effect on hatchability with varying levels of Lactobacillus inoculation. The data presented in Table 1 for turkeys show that pure cultures of *Lactobacillus reuteri* can be successfully introduced into viable poultry eggs without effecting the hatchability of the eggs. The percentage hatchability was unaffected by this inoculation. Similar results are obtained for chickens.

TABLE 1

| TREATMENT | % LIVE EMBRYOS AT HATCH | % OF SURVIVORS AT DAY 7 |
|---|---|---|
| Untreated embryos | 96 | 81 |
| Phosphate injected (control) | 97 | 81 |
| *L. reuteri* air cell injected, $10^5$ CFU | 98 | 85 |
| *L. reuteri* air cell injected, $10^7$ CFU | 100 | 78 |
| *L. reuteri* air cell injected, $10^9$ CFU | 94 | 83 |

This in ovo method serves as a new means for introducing defined beneficial microorganisms such as a pure strain of *Lactobacillus reuteri*, into the gastrointestinal tract of poultry at an early stage. The embryonic chick or poult is immersed in amniotic fluid which is in contact with the gastrointestinal tract. Thus, the microorganism inoculated in ovo can become established in the bird's gastrointestinal tract.

The data presented in Table 2 show that the birds thus inoculated in ovo with *Lactobacillus reuteri* in fact have this microorganism in their gastrointestinal tract when they hatch. In this example the total number of lactobacilli found in the bird's cecum was determined for each treatment. Also determined was the percent of these lactobacilli which were *L. reuteri* as identified by this species' ability to produce the inhibiting agent, reuterin.

The number of total lactobacilli present was determined as colony forming units (CFU) per excised and homogenized cecum using solid (1.5% Agar) Lactobacillus Selection Medium (LBS) as described in references 2, 5, and 7. The percent of these colonies which were *L. reuteri* was determined as described in international patent application PCT/US88/01423, but using *L. plantarum* as the indicator organism. In this test, colonies of lactobacilli on the LBS agar medium are overlaid with 10 ml of 1% liquified agar containing 0.5M glycerol and a *L. plantarum* inoculum. After anaerobic (GasPack System) incubation at 37° C. for 24 hours, zones of growth inhibition are seen around colonies that produce reuterin from glycerol. These colonies are thus identified and enumerated as *L. reuteri*.

Table 2 shows the total lactobacilli found at hatch and the percent of these that were *L. reuteri*. It can be seen in column 1 of Table 2 that control treatments (untreated and phosphate injected) yielded hatchlings with no *L. reuteri* in their ceca although a few other lactobacilli could be found. When the treatments included the different inoculum levels of *L. reuteri*, this microorganism could be found in all the ceca, constituting 33% of the colonies isolated.

TABLE 2

| TREATMENT | Total lactobacilli (CFU/cecum) | % *L. reuteri* |
|---|---|---|
| Untreated embryos | $3.3 \times 10^2$ | 0 |
| Phosphate injected | $<5.0 \times 10^1$ | 0 |
| *L. reuteri* ($10^5$ CFU), air cell, injected | $3.3 \times 10^5$ | 33 |
| *L. reuteri* ($10^7$ CFU), air cell injected | $1.2 \times 10^6$ | 33 |
| *L. reuteri* ($10^8$ CFU), air cell injected | $4.7 \times 10^5$ | 33 |

While the invention has been described with reference to specific embodiments thereof, it will be appreciated that numerous variations, modifications, and embodiments are possible, and accordingly all such variations, modifications, and embodiments are to be regarded as being within the spirit and scope of the invention.

REFERENCES

1. Axelsson L., Lindgren S. E. 1987. Characterization and DNA homology of *Lactobacillus reuteri* strains isolated from pig intestine. J. Appl. Bacteriol., 62:433–440.
2. Axelsson L., Chung T. C., Dobrogosz W. J., Lindgren S. E. 1989. Production of a broad spectrum antimicrobial substance by *Lactobacillus reuteri*. Microbial Ecol. Health Dis., 2:131–136.
3. Bechman T. L., Chambers J. V., Cunningham M. D.. 1977. Influence of *Lactobacillus acidophilus* on performance of young diary calves. J. Dairy Sci., 60:74(abs).
4. Bruce B. B., Gilliland S. E., Bush L. J., Staley T. E. 1979. Influence of feeding cells of *Lactobacillus acidophilus* on the fecal flora of young calves. Oklahoma Anim. Sci. Res. Rep., 207.
5. Chung T. C., Axelsson L., Lindgren Se, Dobrogosz W. J. 1989. In vitro studies on reuterin synthesis by *Lactobacillus reuteri*. Microbial Ecol. Health Dis., 2:137–144.
6. Dellaglio F., Arrizza F. S., Leda A. 1981. Classification of citrate fermenting lactobacilli isolated from lamb stomach, sheep milk and pecorino romano Cheese. Zbl. Bakt. Hyg., Abt. Orig. C2: 349–356.
7. Dobrogosz, W. J., Casas I. A., Pagano G. A. , Talarico T. L., Sjorberg B-M, Karlson M. 1989. *Lactobacillus reuteri* and the enteric microbiota. In: The Regulatory and Protective Role of the Normal Microflora (Eds: GrubbR, MidtvedtT, NorinE.) Macmillan LTD, London, pp. 283–292.
8. Ellinger D. K., Muller L. D., Gantz P. J. 1978. Influence of feeding fermented colostrum and *Lactobacillus acidophilus* on fecal flora and selected blood parameters of young dairy calves. J. Dairy Sci., 61:162(abs).
9. Food and Drug Administration Compliance Policy Guide No. 7126.41, May 2, 1988.
10. Fox S. M. 1988. Probiotics: Intestinal inoculants for production animals. Food-Animal Practice, Vet. Med., August issue.
11. Fuller R. 1986. Probiotics. J. Appl. Bacteriol. Symp. Suppl., 1S–7S.
12. Goodenough E. R., Kleyn D. H. 1976. Influence of viable yoghurt microflora on the digestion of lactose by the rat. J. Dairy Sci., 59: 601–606.
13. Hatch R. C., Thomas R. O., Thayne W. V. 1973. Effect of adding *Bacillus acidophilus* to milk fed to baby calves. J. Dairy Sci., 56:682(abs).
14. Kandler O., Stetter K., Kohl R. 1980. *Lactobacillus reuteri* sp. nov. a new species of heterofermentative lactobacilli. Zbl. Bakt. Hyg. Abt. Orig. C1:264–269.
15. Kandler O., Weiss N., 1986. Regular nonsporing Gram positive rods. Bergey's Manual of Systematic Bacteriology (Eds.: Sneath D. H. A., Mair N. C., Sharpe M. E., Holt J. H.), vol. 2:1208–1234. Williams and Wilkins, N.Y.
16. Metchnikoff E. 1907. Prolongation of Life. Heinemann, London.
17. Morrill J. L., Dayton A. D., Mickelson R. 1977. Cultured milks and antibiotics for young calves. J. Dairy Sci., 60:1105.
18. Muralidhara K. S., Sheggeby G. G., Elliker P. R., England D. C., Sandine W. E. 1977. Effects of feeding lactobacilli on the coliform and Lactobacillus flora of intestine tissue and feces from piglets. J. Food Protection, 40:288–295.
19. Orla-Jensen S. 1943. The lactic acid bacteria. Det Kongelige Danske Videnskasbernes Selskab. Biologiske Skrifter, Bind II, Nr. 3. Kobenhavn.
20. Parker R. B. 1974. Probiotics, the other half of the antibiotic story. Anim. Nutr. Health. 29:4–8.
21. Parkhurst C. R., Edens F. W., Casas I. A. 1991. *Lactobacillus reuteri* and whey reduce Salmonella colonization in turkey poults. International Poultry Trade Show, Southeastern Poultry and Egg Association, Atlanta, Ga., Abs. Sci. Meet., Jan. 30–Feb. 1, 1991.
22. REVUE: Scientifique et Technique, Digestive Microflora and Bioregulation, International Office Of Epizootics, F- 75017, Paris, France, Vol., 8, June, 1989.
23. Sarra P. G., Magri M., Bottazzi V., Dellaglio F., Bosi E. 1979. Frequenza di bacilli heterofementanti nelle feci di vitelli lattanti. Arch. Vet. Ital., 30-16-21.
24. Sarra P. G., Dellaglio F., Bottazzi V. 1985. Taxonomy of lactobacilli isolated from the alimentary tract of chickens. System. Appl. Microbiol., 6:86–89.
25. Sarra P. G., Vescovo M., Fulgoni M. 1986. Study on crop adhesion genetic determinant in *Lactobacillus reuteri*. Microbiologica, 9:279–285.
26. Sissons J. W. 1989. Potential of probiotic organisms to prevent diarrhoea and promote digestion in farm animals—a review. J. Sci. Food Agric., 46:1–13.
27. Speck ML. 1977. Heated yoghurt—is it still yoghurt? J. Food Protection. 40:863–865.
28. Talarico T. L., Casas I. A., Chung T. C., Dobrogosz W. J. 1988. Production and isolation of reuterin: a growth inhibitor produced by *Lactobacillus reuteri*. Antimicrob. Agents. Chemotherap., 32:1854–1858.
29. Talarico T. L., Dobrogosz W. J. 1989. Chemical characterization of an antimicrobial substance produced by *Lactobacillus reuteri*. Antimicrob. Agents Chemotherap., 33:674–679.
30. Talarico T. L., Dobrogosz W. J. 1990. Purification and characterization of glycerol dehydratase from *Lactobacillus reuteri*. Appl. Environ. Microbiol., 56:1195–1197.
31. Talarico Tl, Axelsson L., Novotny J., Fiuzat M., Dobrogosz W. J. 1990. Utilization of glycerol as a hydrogen acceptor by *Lactobacillus reuteri:* Purification of 1,3-propanediol:NAD oxidoreductase. Appl. Environ. Microbiol., 56:943–948.
32. Underdahl N. R., Torres-Medina A., Doster A. R. 1982. Effect of Streptococcus faecium C-68 in control of *Escherichia coli*-induced diarrhoea in gnotobiotic pigs. Amer. J. Vet. Res., 43:2227–2232.
33. Vescovo M., Morelli L., Cocconcelli P. S., Bottazzi V. 1984. Protoplast formation, regeneration, and plasmid curing in Lactobacillus reuteri. FEMS Microbiol. Lett., 23:333–334.

What is claimed is:

1. A method for delivering a direct feed microorganism into the gastrointestinal tract of an avian organism comprising, injecting about $10^5$ to about $10^8$ CFU of a viable, biologically pure culture of *Lactobacillus reuteri* into the air cell of an egg of said avian organism prior to hatching of the egg, wherein said method results in no more than a 2% reduction in hatchability of the egg as compared to an untreated control.

2. A method according to claim 1, wherein the avian organism is a chicken.

3. A method according to claim 1, wherein the avian organism is a turkey.

* * * * *